(12) United States Patent
Dorshow et al.

(10) Patent No.: US 6,228,344 B1
(45) Date of Patent: May 8, 2001

(54) METHOD OF MEASURING PHYSIOLOGICAL FUNCTION

(75) Inventors: Richard Bradley Dorshow, St. Louis; Samuel Achilefu, Bridgeton; Raghavan Rajagopalan, Maryland Heights; Joseph Edward Bugaj, St. Charles, all of MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/258,148

(22) Filed: Feb. 26, 1999

Related U.S. Application Data (63) Continuation-in-part of application No. 08/816,332, filed on Mar. 13, 1997, now Pat. No. 5,928,625.

(51) Int. Cl.$^7$ .......................... A61K 49/00; G01N 31/00
(52) U.S. Cl. ........................... 424/9.1; 424/1.11; 424/9.6
(58) Field of Search ..................... 424/1.11, 9.1, 424/9.3, 9.2, 9.4, 9.5, 9.6, 9.8, 9.7; 436/172

(56) References Cited

U.S. PATENT DOCUMENTS

| | | |
|---|---|---|
| 4,848,349 | 7/1989 | Sherman et al. . |
| 4,905,703 | 3/1990 | Kanda et al. . |
| 5,054,915 | 10/1991 | Kanda et al. . |
| 5,054,916 | 10/1991 | Kanda et al. . |
| 5,178,141 | 1/1993 | Kanda . |
| 5,301,673 | 4/1994 | Rabito et al. . |
| 5,458,128 | 10/1995 | Polanyi et al. . |
| 5,647,363 | 7/1997 | Rabito et al. . |
| 5,928,625 | * 7/1999 | Dorshow et al. ...................... 424/9.1 |

FOREIGN PATENT DOCUMENTS

| | | |
|---|---|---|
| 4445065 | 6/1996 | (DE) . |
| 9706829 | 2/1997 | (WO) . |

OTHER PUBLICATIONS

Awazu, K. et al. "The data processing function of the ICG clearance meter", 1992; Abstract—1 page.
Bilheimer, D.W. et al. "Metabolic Studies in Familial Hypercholesterolemia", *J. Clin. Invest.*, Aug. 1979; 64:524–533.
Graham, B.H. et al. "Serial quantitative skin surface fluorescence: A new method for postoperative monitoring of vascular perfusion in revascularized digits", *The Journal of Hand Surgery*, 1985; 10A:226–30.
Caesar, J. et al. "The Use of Indocyanine Green in the Measurement of Hepatic Blood Flow and as a Test of Hepatic Function", *Clin. Sci.*, 1961; 21:43–57.
Flock, S. T. et al. "Optical Properties of Intralipid: A Phantom Medium for Light Propagation Studies", *Lasers in Surgery and Medicine*, 1992; 12:510–519.
Hemming, A.W. et al. "Indocyanine Green Clearance as a Predictor of Successful Hepatic Resection in Cirrhotic Patients", *The American Journal of Surgery*, May 1992; 163:515–518.

Hollins, B. et al. "Fluorometric Determination of Indocyanine Green in Plasma", *Clin. Chem.*, 1987; 33(6):765–768.
Jalan, R. et al. "Review article: quantitative tests of liver function", *Aliment Pharmacol. Ther.*, 1995; 9:263–270.
Kanaya, N. et al. "Comparison of the effects of sevoflurane, isoflurane and halothane on indocyanine green clearance", *British Journal of Anaesthesia*, 1995; 74:164–167.
Kanaya, N. et al. "Noninvasive ICG clearance test for estimating hepatic blood flow during halothane and isoflurane anaesthesia", *Can. J. Anaesth.*, 1995; 42(3):209–212.
Kanda, M. et al. "Continuous monitoring of Cardiogreen removal by a diseased liver using an optical sensor", *SPIE*, 1988; 904:39–46.
Kudo, M. et al. "Receptor Index via Hepatic Asialoglycoprotein Receptor Imaging: Correlation with Chronic Hepatocellular Damage", *American Journal of Gastroenterology*, 1992; 87(7):865–870.
Li, X. et al. "Tumor Localization Using Fluorescence of Indocyanine Green (ICG) in Rat Models", *SPIE*, 1995; vol. 2389, pp. 789–797.
Mordon, S. et al. "Fluorescence measurement of diode (805nm) laser–induced release of 5,6–CF from DSPC liposomes for monitoring of temperature: an in–vivo study in rat liver using indocyanine green potentiation", *SPIE*, 1995; vol. 2391, pp. 475–483.
Nakayama, M. et al. "Efffects of Ephedrine on Indocyanine Green Clearance During Spinal Anesthesia: Evaluation by the Finger Piece Method", *Anesth. Analg.*, 1993; 77:947–949.
O'Leary, M.A. et al. "Reradiation and imaging of diffuse photon density waves using fluorescent inhomogeneities", *Journal of Luminescence*, 1994; 60&61:281–286.
Ott, P. et al. "Plasma Elimination of Indocyanine Green in the Intact Pig Aftre Bolus Injection and During Constant Infusion: Comparison of Spectrophotometry and High–pressure Liquid Chromatography for Concentration Analysis", *Hepatology*, 1993; 18(6):1504–1515.
Scott, V.L. et al. "Comparison of indocyanine green clearance using serum spectrophotometric analysis and a non–invasive pulse–spectrometry probe in patients with liver failure", Annual Meeting of the American Society of Anesthesiologists, San Diego, CA, Oct. 18–22, 1997, 1 page Abstract.
Sheridan, R.L. et al. "Burn Depth Estimation by Use of Indocyanine Green Fluorescence: Initial Human Trial", *J. Burn Care Rehabil.*, 1995; 16:602–604.

(List continued on next page.)

Primary Examiner—Dameron L. Jones
(74) *Attorney, Agent, or Firm*—Rothwell, Figg, Ernst & Manbeck (57) ABSTRACT

A method of measuring physiological function of a group of body cells, includes the step of selecting a detectable agent capable of emitting a measurable electromagnetic emission. The agent is introduced into body fluid wich contacts the group of body cells. The emission is measured, and physiological function is determined based on measurement of the emission.

20 Claims, 11 Drawing Sheets

OTHER PUBLICATIONS

Shimizu, S. et al. "New Method for Measuring ICG Rmax with a Clearance Meter", *World J. Surg.*, 1995; 19:113–118.

Shinohara, H. et al. "Direct Measurement of Hepatic Indocyanine Green Clearance With Near–Infrared Spectroscopy: Separate Evaluation of Uptake and Removal", *Hepatology*, 1996; 23:137–144.

Soulie, S. et al. "In vivo pharmacokinetic study of two fluorescein derivatives by fluorescence spectroscopy", *SPIE*, 1995; vol. 2627, pp. 109–117.

Tsai, K.-N. et al. "Comparison of ICG Finger Monitor system with conventional blood sampling ICG clearance test in patients with acute severe hepatitis", *Gastroenterological Journal of Taiwan*, 1996; 1 page Abstract.

Urata, K. et al. "Clinical evaluation of indocyanine green clearance using the finger–piece method in patients undergoing hepatic surgery", 1992; 1 page Abstract, Yakuri to Chiryo, 20/10.

* cited by examiner

METHOD OF MEASURING PHYSIOLOGICAL FUNCTION

This application is a continuation-in-part of U.S. Ser. No. 8/816,332, filed Mar. 13, 1997, now U.S. Pat. No. 5,928,625

BACKGROUND OF THE INVENTION

1. Field of the Invention

The present invention is in the field of measuring physiological function of a group of body cells.

2. Description of the Background Art

Current clinical practice for determining liver function includes deriving a CTC score, which is a compilation of laboratory data and clinical assessment of ascites and encephalopathy. D. A. Noe and R. C. Rock (eds), *Laboratory Medicine, The Selection and Interpretation of clinical Laboratory Studies*, Williams and Wilkins, 1994, Baltimore, Md., Chapter 5, *Assessment of Organ Function*, by D. A. Noe, p. 55–60, Chapter 19, *Liver and Biliary Tract*, by A. T. Blei, p. 363–379, Chapter 21, *The Kidneys*, by D. A. Oken and A. C. Schoolwerth, p. 401–410.

Another test involves the use of indocyanine green (ICG). ICG is known to be exclusively cleared from the bloodstream by the liver. Thus a measurement of the ICG blood clearance time profile is directly related to liver function. J. Caesar, S. Shaldon, L. Chiandussi, L. Guevara, and Sheila Sherlock, "The use of indocyanine green in the measurement of hepatic blood flow and as a test of hepatic function," *Clin. Sci.* 21, 43–57 (1961).

The ICG test has undergone an evolution in technology. In its first incarnation, blood was withdrawn from the subject at several times following an IV bolus injection. The blood samples were then processed spectrophotometrically to determine ICG concentration. R. Jalan and P. C. Hayes, "Review article: quantitative tests of liver function," *Aliment Pharmacol. Ther.* 9, 263–270 (1995); A. W. Hemming, C. H. Scudamore, C. R. Shackleton, M. Pudek, and S. R. Erb, "Indocyanine green clearance as a predictor of successful hepatic resection in cirrhotic patients," *Am. J. Surg.* 163, 515–518 (1992); P. Ott, S. Keiding, and L. Bass, "Plasma elimination of indocyanine green in the intact pig after bolus injection and during constant infusion: comparison of spectrophotometry and high-pressure liquid chromatography for concentration analysis," *Hepatology* 18, 1504–1515 (1993). Subsequently, a non-invasive technique employing ear densitometry was developed. C. M. Leevy, F. Smith, J. Longueville, G. Paumgartner, and M. M. Howard, "Indocyanine green clearance as a test for hepatic function: Evaluation by dichromatic ear densitometry," *Journal of Medicine* 24, 10–27 (1993). Problems associated with the clinical development of this device recently led Japanese researchers to improve upon the ear densitometry technique. This newer method, termed the finger-piece method, employs transmitted light of two wavelengths measured throughout a finger to deduce ICG concentration. M. Kanda, K. Taniguchi, K. Awazu, Y. Ishigami, M. Masuzawa, and H. Abe, "Continuous monitoring of Cardiogreen removal by a diseased liver using an optical sensor," *Proc. SPIE* 904, 39–46 (1988); M. Nakayama, N. Kanaya, S. Fujita, and A. Namiki, "Effects of ephedrine on indocyanine green clearance during spinal anesthesia: Evaluation by the finger piece method," *Anesth. Analg.* 77, 947–949 (1993); N. Kanaya, H. Iwasaki, and A. Namiki, "Noninvasive ICG clearance test for estimating hepatic blood flow during halothane and isoflurane anaesthesia," *Can. J. Anaesth.* 42, 209–212 (1995); N. Kanaya, M. Nakayama, S. Fujita, and A. Namiki, "Comparison of the effects of sevoflurane, isoflurane and halothane on indocyanine green clearance," *Br. J. Anaesth.* 74, 164–167 (1995); S. Shimizu, W. Kamiike, N. Hatanaka, Y. Yoshida, K. Tagawa, M. Miyata, and H. Matsuda, "New method for measuring ICG $R_{max}$ with a clearance meter," *World J. Surg.* 19, 113–118 (1995).

Both ear densitometry and the finger-piece method involve measuring absorption (or transmission) of light by ICG.

Also of interest is that in vitro fluorometric determination of ICG in plasma has been demonstrated, B. Hollins, B. Noe, and J. M. Henderson, "Fluorometric determination of indocyanine green in plasma," *Clin. Chem.* 33, 765–768 (1987).

Other references of general interest include: R. L. Sheridan, et al., "Burn depth estimation by indocyanine green fluorescence: Initial human trial," *Journal of Burn Care & Rehabilitation* 16, 602–604 (1995); M. A. O'Leary, D. A. Boas, B. Chance, and A. G. Yodh, "Reradiation and imaging of diffuse photon density waves using fluorescent inhomogeneities," *Journal of Luminescence* 60 & 61, 281–286 (1994); X. Li, B. Beauvoit, R. White, S. Nioka, B. Chance, and A. Yodh, "Tumor localization using fluorescence of indocyanine green (ICG) in rat models," *Proc. SPIE* 2389, 789–797 (1995).

There remains a need in the art for improved methods of measuring physiological function.

SUMMARY OF THE INVENTION

In accordance with the present invention, a method of measuring physiological function of a group of body cells, includes the step of selecting a detectable agent capable of emitting a measurable member comprising an electromagnetic emission. The agent is introduced into body fluid which contacts the group of body cells. The emission is measured, and physiological function is determined based on measurement of the emission. The emission can be measured using non-invasive or invasive techniques. Invasive techniques include using endoscopes and catheters inserted into the respective body portion. Non-invasive techniques include surface probes such as ear clips and finger probes.

DETAILED DESCRIPTION OF THE INVENTION

In accordance with one embodiment of the present invention, a method is disclosed for determining cell and/or organ function by measuring the blood pool clearance of a targeted agent, sometimes referred to herein as tracer. The cell and/or organ function can be determined by the rate these cells remove the tracer from the bloodstream. Function can also be assessed by measuring the rate the cells of interest accumulate the tracer or convert it into an active or other form.

The agent may be targeted to a group of cells or organ which is a high capacity clearance system. The agent may contain a chromophore and/or fluorophore.

For agents containing chromophores and/or fluorophores, blood pool clearance may be measured using a light source/photocell device that measures tissue absorbance or fluorescence in a non-target site, such as an ear lobe, finger, brain or retina. Accumulation of the tracer within the cells of interest can be assessed in a similar fashion. The detection of such accumulation can be facilitated by using fluorophores which emit in the near infrared wavelengths since body tissues are relatively transparent at these wavelengths.

The agent may be introduced into the patient by any suitable method, including intravenous, intraperitoneal or subcutaneous injection or infusion, oral administration, transdermal absorption through the skin, or by inhalation.

The present invention may be used for rapid bedside evaluation of biologic functions. For example, data on cardiac output, cause of hypercholesterolemia, as well as renal and hepatic function, may be obtained in less than sixty minutes at the bedside after a single intravenous injection. In accordance with one embodiment, a patient may receive a bolus injection of a plurality (e.g., three) different compounds, each containing a different agent (e.g., fluorophore).

Cardiac output may be determined utilizing the present invention in conjunction with known methods such as the Fick principle.

Glomerular filtration may be determined by clearance of a low molecular weight fluorescent agent such as fluorescein-succinylated poly-D-Lysine or fluorescein-inulin.

Whether hypercholesterolemia is caused by poor LDL clearance may be determined by analyzing the clearance of fluorescent-labelled LDL. Hepatic function may be assessed by measuring the clearance rate of a fluorescent-labelled asialoglycoprotein or a dye such as indocyanine green.

The present invention includes fluorescence detection of an agent which is cleared from the bloodstream by the kidneys or liver. Thus, assessment of renal or hepatic function by in vivo fluorescence detection is encompassed within the invention. The invention can also be used to monitor the efficiency of hemodialysis.

Tumor cells or brain cells also can be targeted in accordance with the invention.

The clearance of a plurality of separate tracers may be determined simultaneously by selecting excitation wavelengths and filters for the emitted photons. The concentration/time curves may be analyzed in real time by a microprocessor. The resulting clearance rates may be calculated and displayed for immediate clinical impact. In cases where unlabeled competing compounds are present (e.g., LDL, asialoglycoproteins), a single blood sample may be analyzed for the concentration of these competing compounds and the results used to calculate a flux (micromoles/minute) through the clearance pathways.

Figure 1:
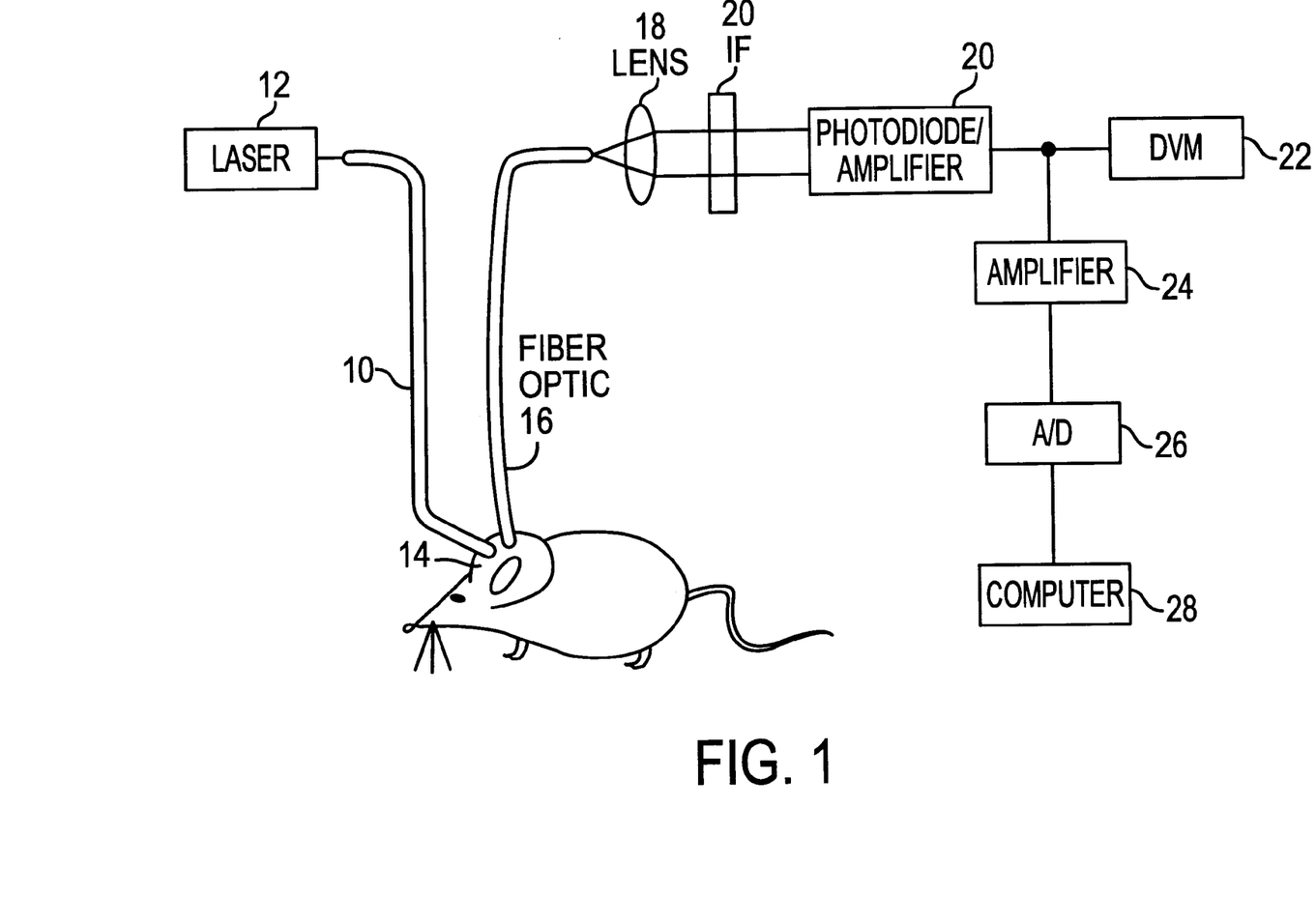
FIG. 1 is a schematic illustration of an in vivo fluorescence detection apparatus in accordance with one embodiment.
Figure 2:
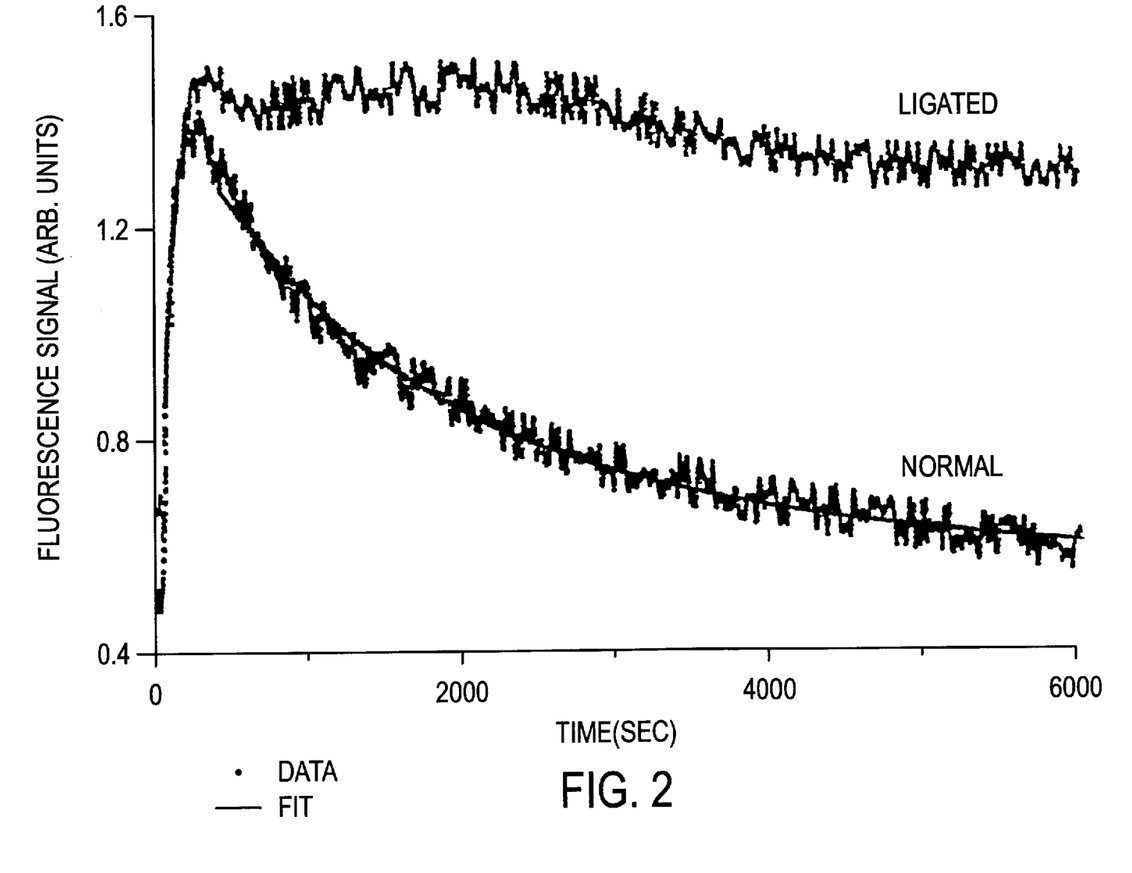
FIG. 2 graphically depicts the in vivo fluorescence time dependence after a bolus injection of FITC labelled succinylated poly-D-Lysine in a single rat pre-kidney ligation (Normal) and post-kidney ligation (Ligated). The solid line is a single exponential fit to the measured data. (Excitation at 488 nm, emission monitored at 518 nm.)

In order to demonstrate utility of the invention, a non-invasive fluorescence detection system in accordance with the present invention was employed to continuously monitor dye removal from the vasculature. Differentiation between normal and abnormal organ function in a rat model was demonstrated for both liver and kidney. With reference to FIG. 1, a fiber optic 10 transmitted light from source 12 to ear 14. A second fiber optic 16 positioned near the ear 14 transmitted the fluorescent light to a detector system 20. Two dyes were employed in this initial study. Indocyanine green is exclusively cleared from the blood stream by the liver, and was excited in vivo with laser light at 780 nm. The fluorescence signal was detected at 830 nm. A characteristic clearance curve of normal hepatic function was obtained. Upon ablation of a portion of the liver, the clearance curve was greatly extended as expected. FITC labelled, succinylated poly-D-lysine was excited in vivo with laser light at 488 nm. The fluorescence signal was detected at 518 nm. A characteristic clearance curve of normal renal function was obtained. Upon ligation of both kidneys, the clearance curve remained elevated and constant, indicating little if any clearance. See FIG. 2.

With the schematic apparatus for non-invasive in vivo detection of fluorescence shown in FIG. 1, for ICG fluorescence detection, a nominal 785 nm collimated solid state laser source was employed (LaserMax Inc. model # LAS-300-780-5). For FITC fluorescence detection, an argon ion laser (Coherent Innova model 90) tuned to the 488 nm line was used. Either laser source was directed into the end of a 3.2 mm inner diameter glass fiber optic bundle 10 (Oriel #77526). The other end of this laser delivery bundle was placed approximately 2 cm from the rat ear 14 at an approximate 45° angle. A second similar fiber optic bundle 16 for use as the fluorescence detection conduit was placed approximately 1 cm from the ear 14 at a 30° angle.

The exit end of the detection fiber bundle 16 was positioned at the focal length of a 20 mm focal length lens 18. The output light was thus collimated after exiting the bundle and passing through the lens. A narrow band interference filter 20 (IF) was the next element in the optics train (CVI Laser Corporation), allowing light of the appropriate wavelength to pass on to the detector 20. For the ICG fluorescence experiment, an 830 nm filter (10 nm FWHM) was used. For the FITC fluorescence experiment, a 518 nm filter (3 nm FWHM) was used.

The detector 20 was a small silicon photodiode (UDT model PIN-10D) connected to a transimpedance amplifier (UDT model 101C). A digital voltmeter 22 (DVM) monitors the output signal. A subsequent voltage amplifier 24

(Tektronix AM-502) boosts the signal if needed. The amplifier output is connected to a National Instruments BNC-2080 breakout board, which is interfaced to a National Instruments DAQ-700 data acquisition board 26 (A/D). LabVIEW® data acquisition software in computer 28 collects the experimental raw data.

The current method contrasts with the prior art methods which used radiolabeled tracers. The present method eliminates concerns about radioactivity and allows concurrent measurements of different parameters simply by rapid alteration of the excitation and emission wavelengths.

A variety of dyes and carriers can be used for the disclosed methods. Dyes which can be used include phenylxanthenes (e.g., fluorescein), phenothiazines, phenoselenazines, cyanines, indocyanines and squaraines. Preferred carriers are physiologically acceptable polyanionic compounds which may be conjugated to the above dyes. Carriers which can be used include polyacrylic acid, polyaspartic acid, polyglutamic acid, polynucleotides, polyarginine, polyserine, polyornithine and polylysine. The following dye-carrier conjugates can be used as part of the present invention with those marked with an "*" being the preferred conjugates. Those preceded by RF are used to test renal function; those preceded by LF are used to test liver function; and those preceded by RF/LF are used to test renal and liver function.

RF Fluorescein-polyaspartic acid*
RF Fluorescein-polyglutamic acid*
RF Fluorescein-polyacrylic acid*
RF Fluorescein-polynucleotides
RF Fluorescein-polynitrophenylalanine
RF Fluorescein-polydinitrophenylalanine
RF Fluorescein-polytrinitrophenylalanine
RF Fluorescein-polysulfonylphenylalanine
RF Fluorescein-polydisulfonylphenylalanine
RF Fluorescein-polytrisulfonylphenylalanine
RF Fluorescein-polysuccinate
RF Fluorescein-polymalonate
RF Fluorescein-polyglutarate
RF Fluorescein-polyglycolate
LF Bis(hexanoic acid)indocyanine green-polyaspartic acid*
LF Bis(hexanoic acid)indocyanine green-polyglutamic acid*
LF Bis(hexanoic acid)indocyanine green-polyacrylic acid*
LF Bis(hexanoic acid)indocyanine green-polynucleotides
LF Bis(hexanoic acid)indocyanine green-polynitrophenylalanine
LF Bis(hexanoic acid)indocyanine green-polydinitrophenylalanine
LF Bis(hexanoic acid)indocyanine green-polytrinitrophenylalanine
LF Bis(hexanoic acid)indocyanine green-polysulfonylphenylalanine
LE Bis(hexanoic acid)indocyanine green-polydisulfonylphenylalanine
LF Bis(hexanoic acid)indocyanine green-polytrisulfonylphenylalanine
LF Bis(hexanoic acid)indocyanine green-polysuccinate
LF Bis(hexanoic acid)indocyanine green-polymalonate
LF Bis(hexanoic acid)indocyanine green-polyglutarate
LF Bis(hexanoic acid)indocyanine green-polyglycolate
RF/LF Bis(propanoic acid)indocyanine green-polyaspartic acid*
RF/LF Bis(propanoic acid)indocyanine green-polyglutamic acid*
RF/LF Bis(propanoic acid)indocyanine green-polyacrylic acid*
RF/LF Bis(propanoic acid)indocyanine green-polynucleotides
RF/LF Bis(propanoic acid)indocyanine green-polynitrophenylalanine
RF/LF Bis(propanoic acid)indocyanine green-polydinitrophenylalanine
RF/LF Bis(propanoic acid)indocyanine green-polytrinitrophenylalanine
RF/LF Bis(propanoic acid)indocyanine green-polysulfonylphenylalanine
RF/LF Bis(propanoic acid)indocyanine green-polydisulfonylphenylalanine
RF/LF Bis(propanoic acid)indocyaninegreen-polytrisulfonylphenylalanine
RF/L: Bis(propanoic acid)indocyanine green-polysuccinate
RF/LF Bis(propanoic acid)indocyanine green-polyscalonate
RF/LF Bis(propanoic acid)indocyanine green-polyglutarate
RF/LF Bis(propanoic acid)indocyanine green-polyglycolate
RF Bis (benzothiazole) squaraine-polyaspartic acid*
RF Bis(benzothiazole)isquaraine-polyglutamic acid*
RF Bis(benzothiazole)squaraine-polyacrylic acid*
RF Bis(benzothiazole)squaraine-polynucleotides
RF Bis(benzothiazole)squaraine-polynitrophenylalanine
RF Bis(benzothiazole)squaraine-polydinitrophenylalanine
RF Bis(benzothiazole)squaraine-polytrinitrophenylalanine
RF Bis(benzothiazole)squaraine-polysulfonylphenylalanine
RF Bis(benzothiazole)squaraine-polydisulfonylphenylalanine
RF Bis(benzothiazole)squaraine-polytrisulfonylphenylalanine
RF Bis(benzothiazole)squaraine-polysuccinate
RF Bis(benzothiazole)squaraine-polymalonate
RF Bis(benzothiazole)squaraine-polyglutarate
RF Bis(benzothiazole)squaraine-polyglycolate
RF Bis(trihydroxyphenyl)squaraine-polyaspartic acid*
RF Bis(trihydroxyphenyl)squaraine-polyglutamic acid*
RF Bis(trihydroxyphenyl)squaraine-polyacrylic acid*
RF Bis(trihydroxyphenyl)squaraine-polynucleotides
RF Bis(trihydroxyphenyl)squaraine-polynitrophenylalanine
RF Bis(trihydroxyphenyl)squaraine-polydinitrophenylalanine
R. Bis(trihydroxyphenyl)squaraine-polytrinitrophenylalanine
RF Bis(trihydroxyphenyl)squaraine-polysulfonylphenylalanine
RF Bis(trihydroxyphenyl)squaraine-polydisulfonylphenylalanine
RF Bis(trihydroxyphenyl)squaraine-polytrisulfonylphenylalanine
RF Bis(trihydroxyphenyl)squaraine-polysuccinate
RF Bis(trihydroxyphenyl)squaraine-polymalonate
RF Bis(trihydroxyphenyl)squaraine-polyglutarate
RF Bis(trihydroxyphenyl)squaraine-polyglycolate The invention is further illustrated by the following examples, which are not intended to be limiting.

EXAMPLE 1

For these in-vivo studies, normal Sprague-Dawley rats weighing ~250 grams were first anesthetized with urethane (1.35 g/kg) administered via intraperitoneal injection.

After each animal had achieved the desired plane of anesthesia, a small (0.5 cm) incision was made in the upper thorax exposing the left jugular vein. The lobe of the left ear was fixed to a glass microscope slide, and the incident laser light delivered from the fiber optic was centered on that ear. Data acquisition was then initiated, and a background reading of fluorescence was obtained prior to administration of the test article. Next, the dye (ICG for liver clearance assessment, FITC labeled poly-D-lysine for kidney clearance assessment) was administered via the jugular vein. The fluorescence signal immediately increased to a peak value. The signal decayed as a function of time as the dye presumably cleared from the bloodstream.

The anesthetized rat was placed on its back and a midline ventral abdominal skin incision made extending from the xiphoid cartilage to approximately midway to the tail. A similar incision was then made in the abdominal muscles exposing the iver. The rat was repositioned and a bolster placed under the horax to cause the liver to fall slightly forward and away from he diaphragm. The median and left lateral lobes of the liver were gently moved out of the abdominal cavity and placed onto a gauze pad wetted with saline. The two lobes were vertically raised and a 3-0 ligature placed around the isolated lobes but were not ligated at this point of the procedure. The lobes were replaced in the abdominal cavity and the bolster removed. The incision was closed with wound clips.

ICG was administered to the animal via the exposed jugular vein as in the previous study. The clearance of the test article was monitored as before to determine the normal hepatic clearance of the ICG. After the normal clearance curve was obtained, the ligature around the two isolated lobes of the liver was tied securely to effect a partial hepatectomy. The animal was allowed to equilibrate for 20 minutes in this state. The ICG was next administered via the exposed jugular vein, and the clearance of the test article monitored. Clearance curves of normal versus partial hepatectomized animals were obtained for an n=3 sample.

Figure 3:
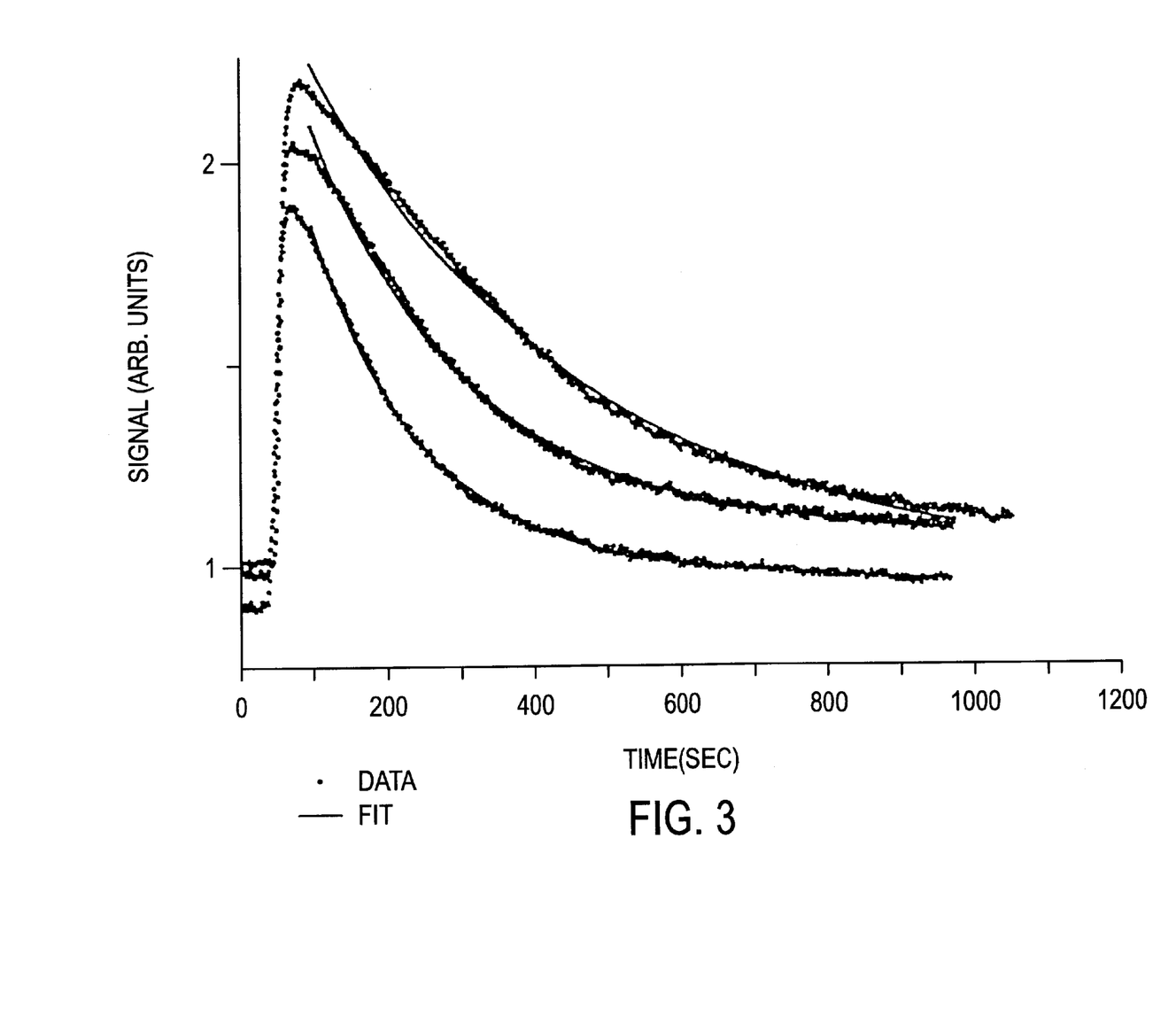
FIG. 3 graphically depicts in vivo fluorescence time dependence for three rats after a bolus injection of ICG. The solid lines are single exponential fits to the measured data.

The time dependence of fluorescence measured at the ear pre and post bolus injection of ICG for three rats is shown in FIG. 3. The data can be described in terms of three stages. Stage 1 consisted of approximately the first 30 seconds of data, which was gathered pre-bolus injection. These data were constant and represented the baseline value for the forthcoming experiment. The value of the baseline should be zero, since no fluorescence is occurring during this stage. Stage 2 occurred several seconds post-injection, the signal rapidly rose to a maximum as the dye reached the ear and equilibrated in the blood pool. In the third stage, the fluorescence signal decayed with time as the liver filtered the ICG out of the blood stream. Visually, the decay rates were similar for all three. After 15 minutes, approximately 90% of the initial signal was lost.

Figure 4:
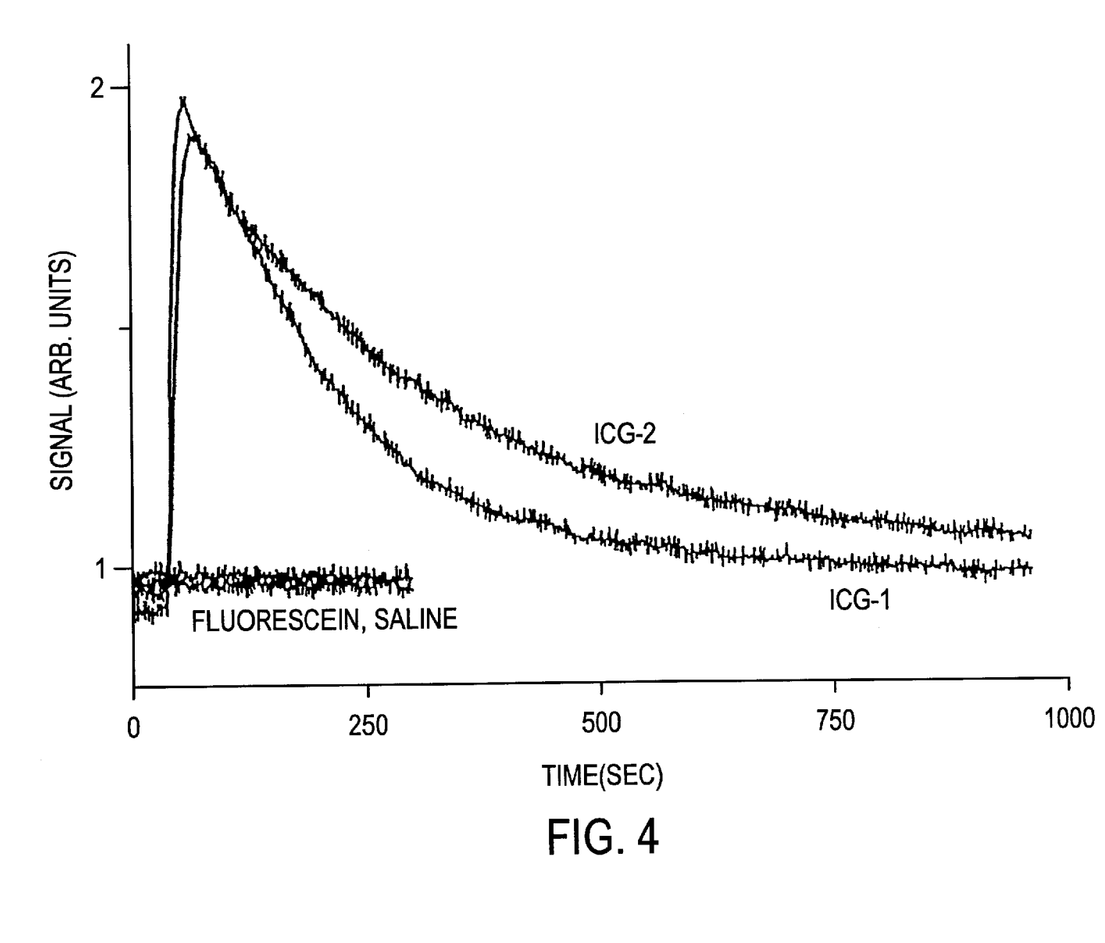
FIG. 4 graphically depicts the in vivo fluorescence time dependence of a succession of bolus injections in one rat. In chronological order: ICG (ICG-1), FITC only, saline only, ICG again (ICG-2).

To verify that the measurement was indeed that of ICG fluorescence, the following control study was performed. A rat was injected, as above, with 500 µL of 1.41 mM ICG. A normal fluorescence time course was obtained and is labeled as ICG-1 in FIG. 4. Then the same rat was injected with 500 µL of 1.41 mM fluorescein (Sigma, St. Louis, Mo.). As shown in FIG. 4, no fluorescence signal was detected. As a further check, 500 µL of saline solution (Baxter, Deerfield, Ill.) was injected into the same rat next. Again, no detectible signal was obtained. Finally, the rat was once again injected with 500 µL of 1.41 mM ICG, and a second "normal" curve was obtained.

Figure 5:
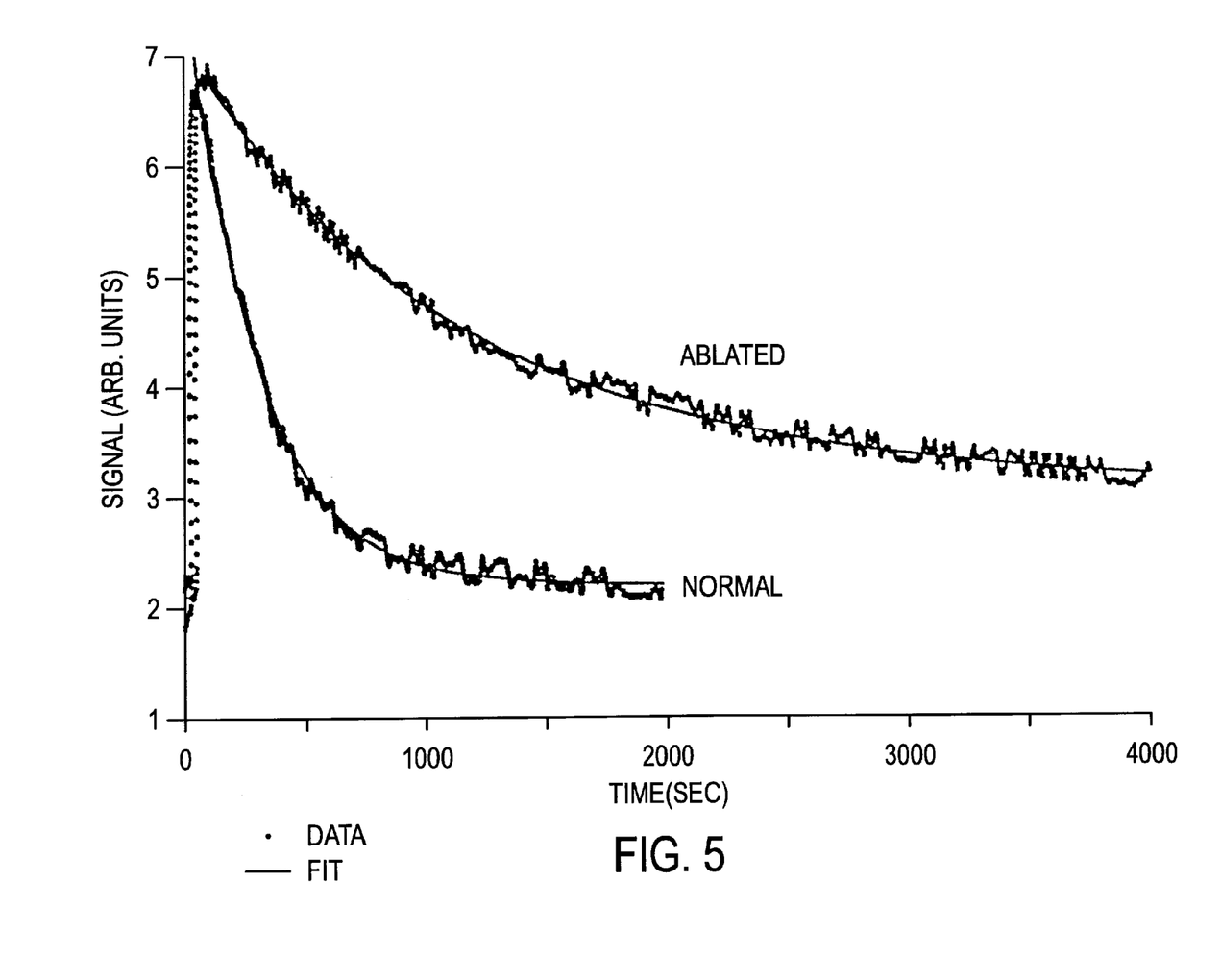
FIG. 5 graphically depicts the in vivo fluorescence time dependence after a bolus injection of ICG in a single rat pre-partial liver ablation (Normal) and post-partial liver ablation (Ablated). The solid lines are single exponential fits to the measured data.

To verify that these fluorescence decay curves were related to liver function, an experiment involving a partial liver ablation was performed. The partial liver ablation procedure is outlined above. Once the surgery was complete, and the ligatures for use in partially ablating the liver were ready, the rat was injected with 500 µL of 1 mM ICG solution. A normal fluorescence time course curve was obtained and is shown in FIG. 5.

The liver was then partially ablated by tightening the ligatures. The rat was allowed to equilibrate for ten minutes. Next, another injection of 500 µL of 1 mM ICG was given. The fluorescence time curve was measured and is also shown in FIG. 5. The capability of the liver to remove ICG from the blood pool was drastically altered, the fluorescence decay rate for the partially ablated liver was much slower than the normal. Upon sacrifice, the liver was weighed and 44% of the liver was found to be ablated.

EXAMPLE 2

500 mg (~125 mole equivalent lysine) poly-D-lysine 4000 (Sigma P-0296) was dissolved in 10 µL 0.1 M $Na_2CO_3$, in a dark glass vial with magnetic stirring bar. 24.3 mg (62.5 µmoles) FITC (Fluorescein isothiocyanate, Sigma F-7250) was dissolved in 1.5 mL DMSO (dimethyl sulfoxide). At 25° C., with stirring, the FITC solution was slowly added to the poly-D-lysine solution. The reaction was allowed to proceed for 30 minutes at 25° C., then transferred to 4° C., and stirred 12 hrs. The fluorescein conjugate was separated from unbound FITC by gel filtration on Sephadex G-25, eluting with 0.9% (w/v) NaCl.

20 mL 0.9% NaCl containing ~30 umoles of the above conjugate were placed in a dark glass vial with magnetic stirring bar and pH electrode at 25° C.; pH was raised to 9.5 by addition of 0.5 M NaOH. 500 mg of succinic anhydride was added slowly, with stirring, to this solution over a period of 30 minutes, maintaining pH 9.5–10.0 by the addition of 0.5 M NaOH. The pH was then allowed to fall to a stable value of 7.5, with a final volume of 27 mL. The reaction mixture was dialyzed vs. 0.9% (w/v) NaCl using a dialysis membrane with 3.5 kd cutoff, and the retained polymer conjugate, at ~4.0 µM fluorescein concentration equivalent, was used directly for infusion.

The anesthetized rat was placed on the ventral surface and bilateral dorsoventral incisions were made in the abdominal cavity near to the coastal border of the thorax. The kidneys were freed of connective tissue and were gently pulled away from the abdomen by grasping the perirenal fat tissue. A single 3-0 ligature was placed around the renal vessels and ureter so as not to occlude collateral vessels. The ligatures were not tied at this point of the procedure.

Succinylated, fluorescein-labeled poly-D-lysine was administered via the exposed jugular vein. The clearance of the test article was monitored as before to determine the normal renal clearance of poly-D-lysine. After the normal clearance curve was obtained, the ligature was tied to effect a total (bilateral) nephrectomy. The animal was allowed to stabilize in this condition for 20 minutes. The test article was next administered via the exposed jugular vein and the clearance of the compound monitored. Clearance curves of normal versus total nephrectomized animals were obtained for an n=3 sample.

EXAMPLE 3

Preparation of Fluorescein-polyaspartic Acid (6000) Conjugate

Figure 6:
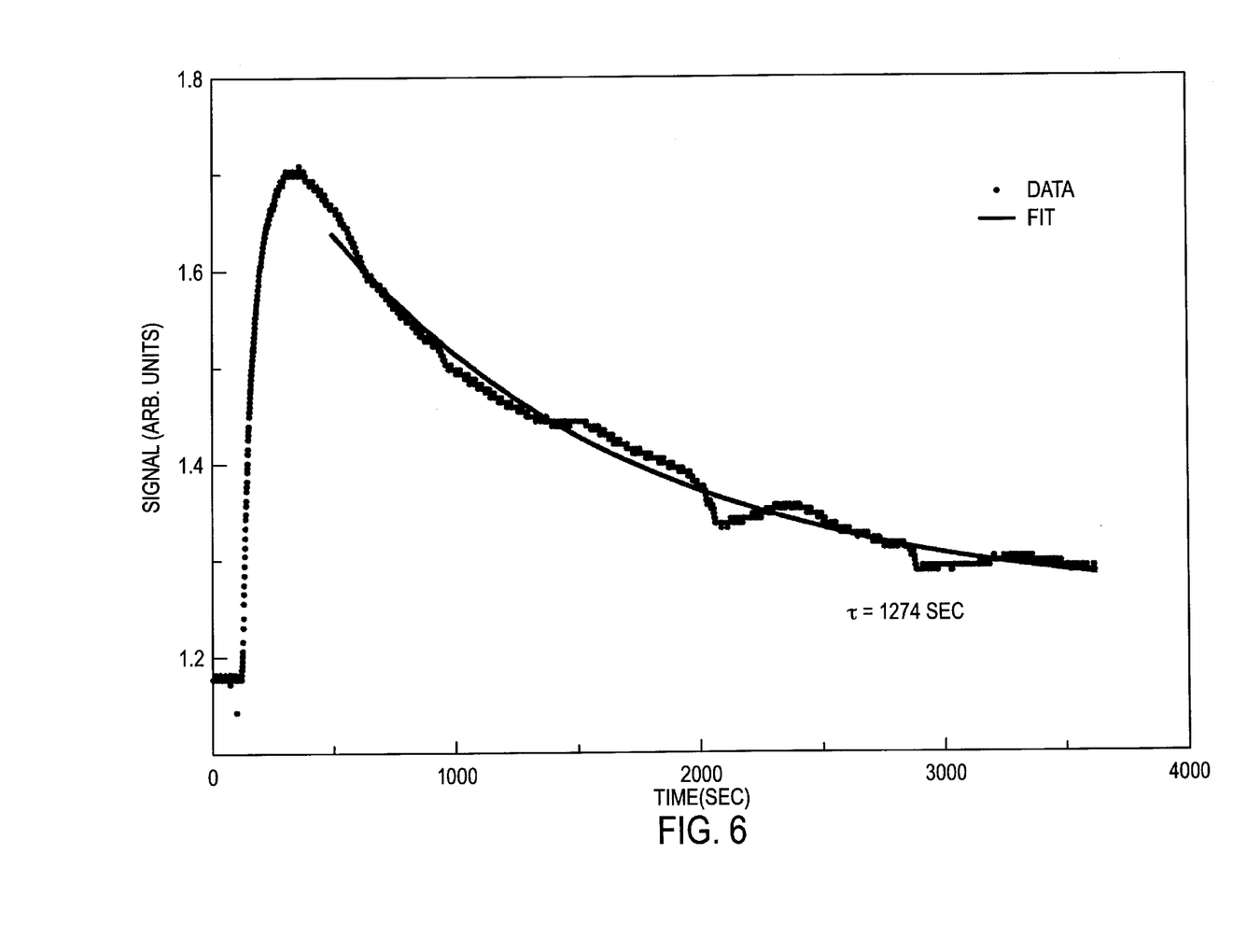
FIG. 6 shows the blood clearance profile of fluorescein-polyaspartic acid (6000) conjugate.

A solution of fluorescein isothiocyanate (20 mg) in DMSO (0.5 mL) was added to a solution of polyaspartic acid (MW: 6000, 180 mg) in water (1 mL). The reddish-orange homogeneous solution was kept at ambient temperature for 24 hours. The reaction mixture was treated with acetone (20 mL). The fine precipitate was separated by centrifugation. The supernatant was discarded and the precipitate resuspended in acetone (10 mL). This washing process was repeated three more times to remove bulk of unreacted fluorescein isothiocyanate. The pellet was dissolved in water (0.5 mL) and chromatographed through Sephadex G-25 (prefilled Pharmacia PD-10) column. One milliliter fractions were collected. The desired fractions (1–4) were pooled and lyophilized to give 87 mg of the desired conjugate as an orange solid. Absorbance of 0.21 mg/mL solution was 0.26, which corresponds to 10.2% conjugation. The procedure of Example 1 was followed using an excitation wavelength of 488 nanometers and an emission wavelength of 520 nanometers. FIG. 6 shows the blood clearance profile of fluorescein-polyaspartic acid (6000) conjugate.

EXAMPLE 4

Preparation of Fluorescein-polyaspartic Acid (10000) Conjugate

Figure 7:
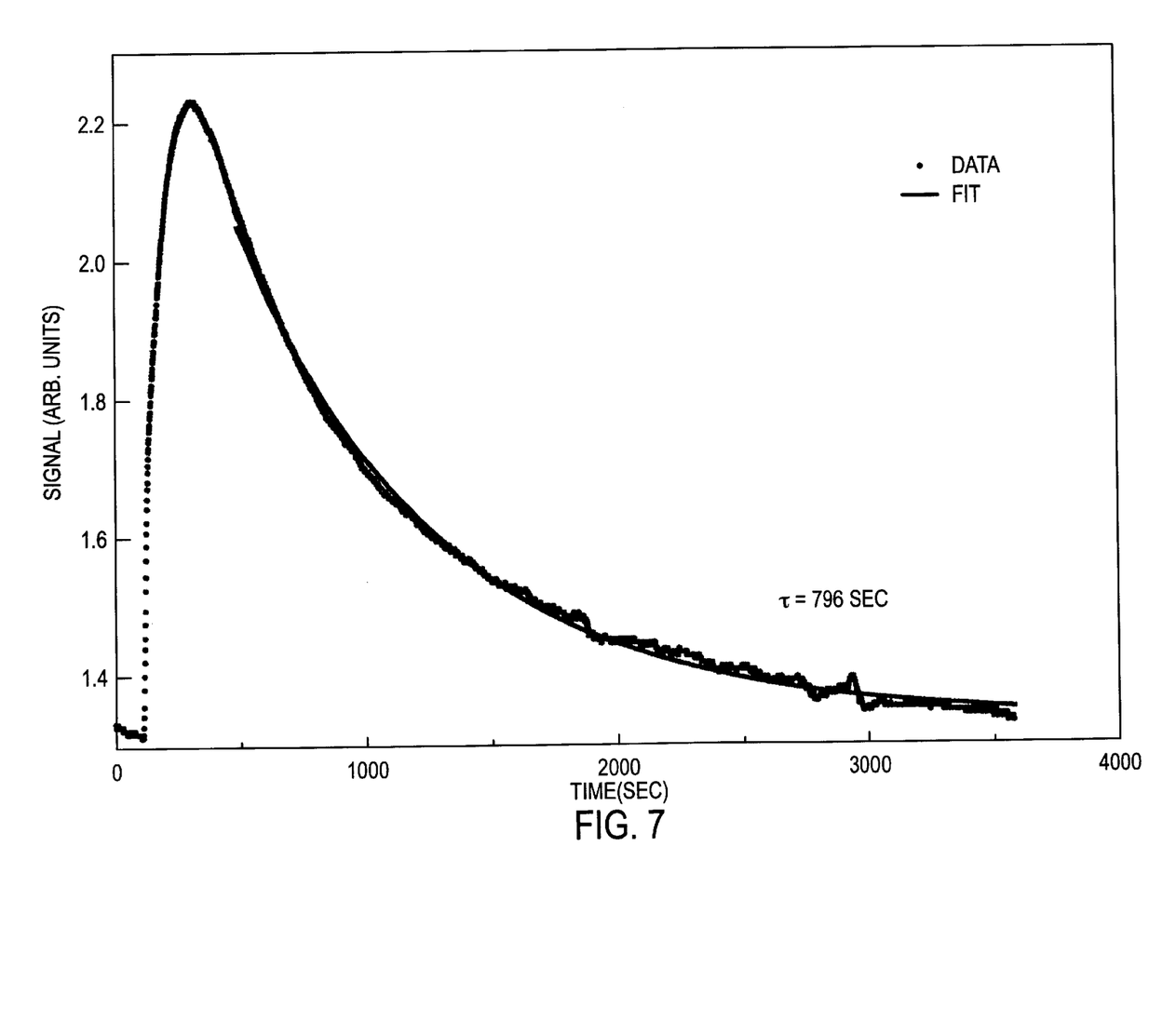
FIG. 7 shows the blood clearance profile of fluorescein-polyaspartic acid (10000) conjugate.

A solution of fluorescein isothiocyanate (20 mg) in DMSO (0.5 mL) was added to a solution of polyaspartic acid (MW: 10000, 180 mg) in water (1 mL). The reddish-orange homogeneous solution was kept at ambient temperature for 24 hours. The reaction mixture was treated with acetone (20 mL). The fine precipitate was separated by centrifugation. The supernatant was discarded and the precipitate resuspended in acetone (10 mL). This washing process was repeated three more times to remove bulk of unreacted fluorescein isothiocyanate. The pellet was dissolved in water (0.5 mL) and chromatographed through Sephadex G-25 (prefilled Pharmacia PD-10) column. The desired fractions (1–4) were pooled and lyophilized to give 100 mg of the desired conjugate as an orange solid. Absorbance of 0.19 mg/mL solution was 0.05, which corresponds to 3.3% conjugation. The procedure of Example 1 was followed using an excitation wavelength of 488 nanometers and an emission wavelength of 520 nanometers. FIG. 7 shows the blood clearance profile of fluorescein-polyaspartic acid (10000) conjugate.

EXAMPLE 5

Preparation of Fluorescein-polyalutamic Acid (13000) Conjugate

Figure 8:
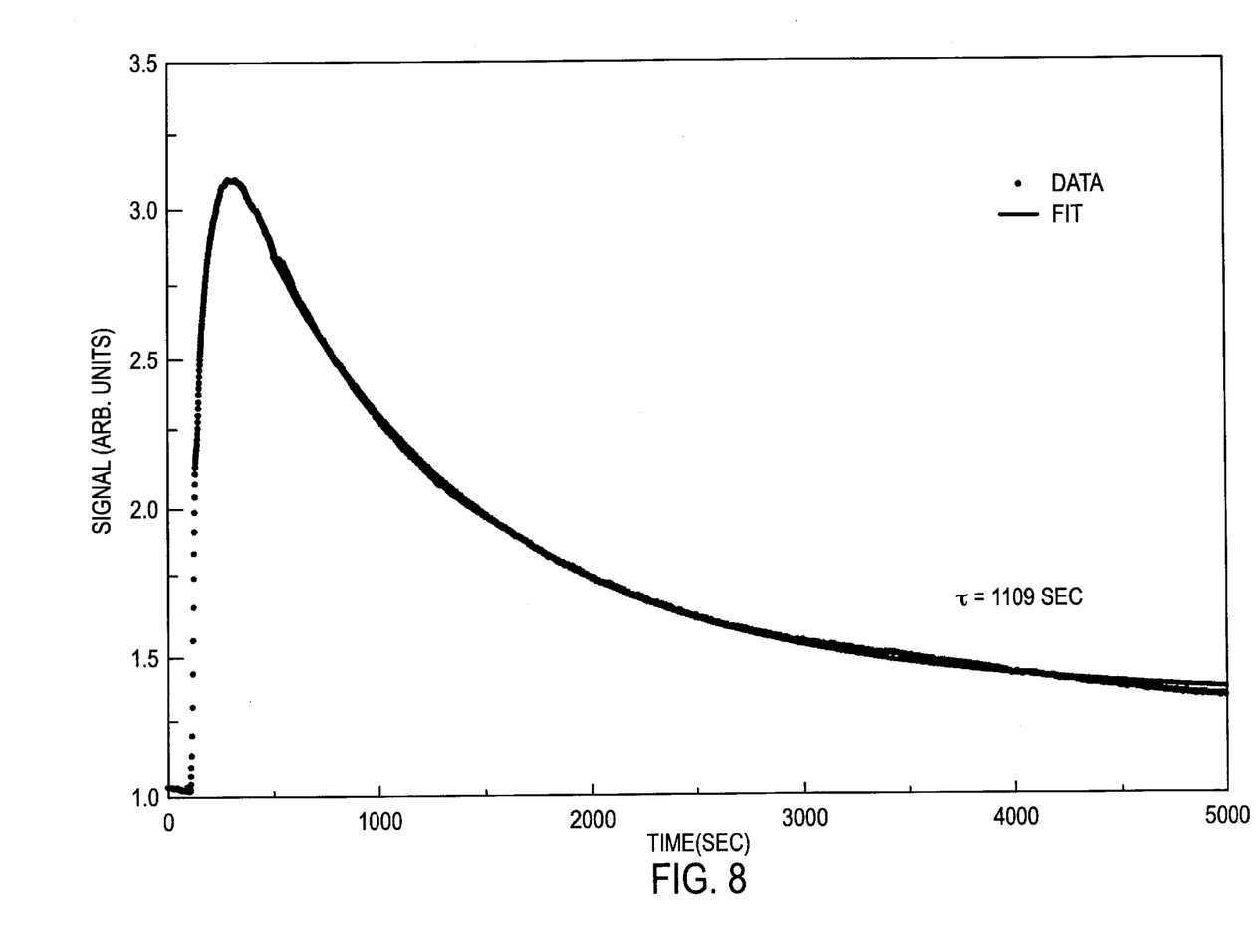
FIG. 8 shows the blood clearance profile of fluorescein-polyglutamic acid (13000) conjugate.

A solution of fluorescein isothiocyanate (20 mg) in DMSO (0.5 mL) was added to a solution of polyglutamic acid (MW: 13000, 150 mg) in water (1 mL). The reddish-orange homogeneous solution was kept at ambient temperature for 24 hours. The reaction mixture was treated with acetone (20 mL). The fine precipitate was separated by centrifugation. The supernatant was discarded and the precipitate resuspended in acetone (10 mL). This washing process was repeated three more times to remove bulk of unreacted fluorescein isothiocyanate. The pellet was dissolved in water (0.5 mL) and chromatographed through Sephadex G-25 (prefilled Pharmacia PD-10) column. The desired fractions (1–4) were pooled and lyophilized to give 80 mg of the desired conjugate as an orange solid. Absorbance of 0.21 mg/mL solution was 0.79, which corresponds to 60.8% conjugation. The procedure of Example 1 was followed using an excitation wavelength of 488 nanometers and an emission wavelength of 520 nanometers. FIG. 8 shows the blood clearance profile of fluorescein-polyglutamic acid (13000) conjugate.

EXAMPLE 6

Preparation of Fluorescein-polyarginine (10000) Conjugate

Figure 9:
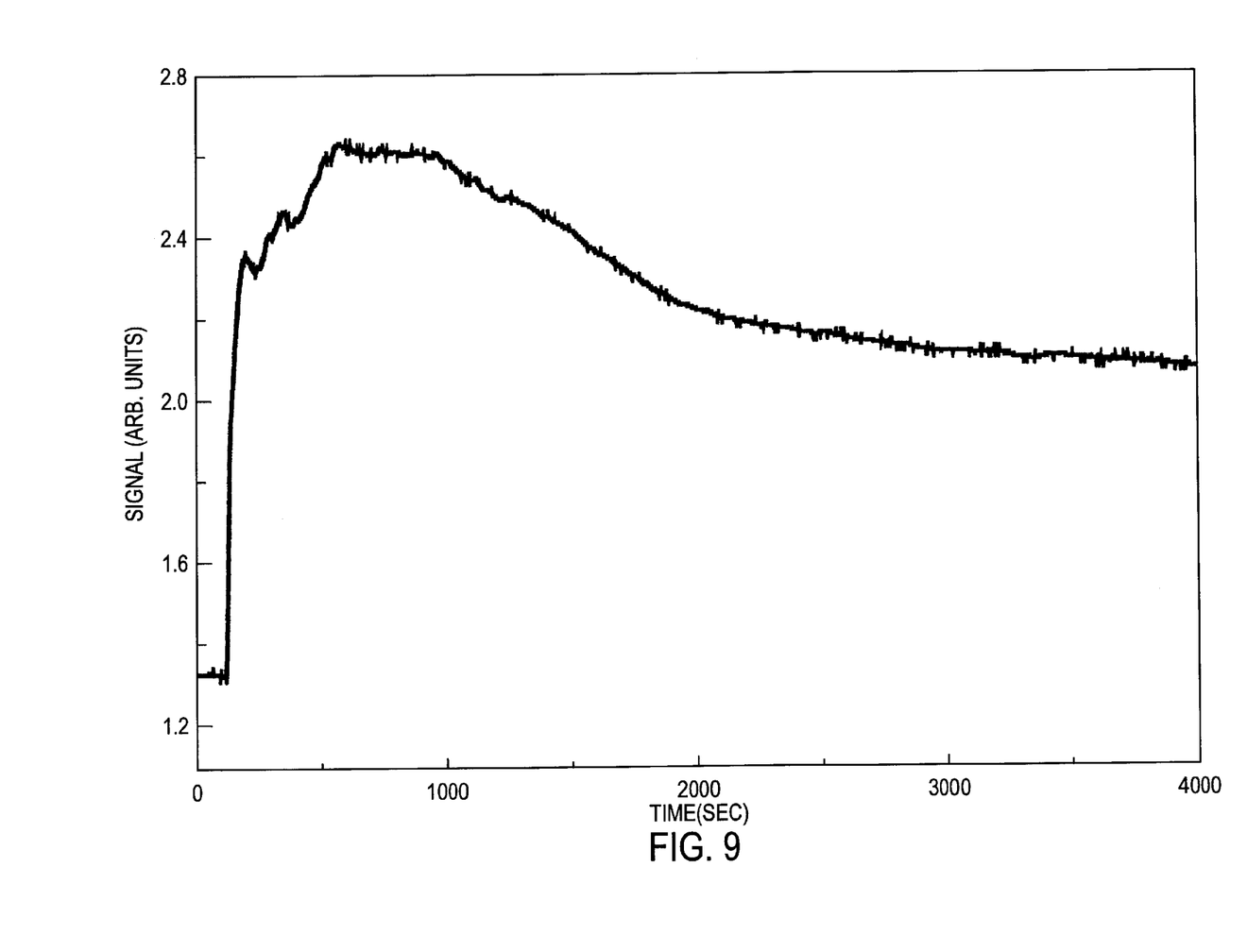
FIG. 9 shows the blood clearance profile of fluorescein-polyarginine (10000) conjugate.

A solution of fluorescein isothiocyanate (20 mg) in DMSO (0.5 mL) was added to a solution of polyarginine (MW: 10000, 150 mg) in water (1 mL). The reddish-orange homogeneous solution was kept at ambient temperature for 24 hours. The reaction mixture was treated with acetone (20 mL). The fine precipitate was separated by centrifugation. The supernatant was discarded and the precipitate resuspended in acetone (10 mL). This washing process was repeated three more times to remove bulk of unreacted fluorescein isothiocyanate. The pellet was dissolved in water (0.5 mL) and chromatographed through Sephadex G-25 (prefilled Pharmacia PD-10) column. The desired fractions (1–4) were pooled and lyophilized to give 80 mg of the desired conjugate as an orange solid. Absorbance of 0.21 mg/mL solution was 0.73, which corresponds to 60.5% conjugation. The procedure of Example 1 was followed using an excitation wavelength of 488 nanometers and an emission wavelength of 520 nanometers. FIG. 9 shows the blood clearance profile of fluorescein-polyarginine (10000) conjugate.

EXAMPLE 7

Preparation of Indocyanine-dodecaaspartic Acid Conjuaate (a) Peptide synthesis: Dodecaaspartic acid mono and bis aspartimide were prepared by solid phase Fmoc peptide synthesis with automated Applied Biosystems 432A Synergy synthesizer. The amino acid units (75 micromoles each) were sequentially activated with a mixture of N-hydroxybenzotriazole (HOBT) and 2-(1H-benzotriazole-1-lyl)-1,1,3,3-tetramethyluronium hexafluorophosphate (HBTU). The Fmoc of the terminal amino acid was removed with 20% piperidine in dimethylformamide.

(b) Dye synthesis: The near infrared absorbing bis (carboxyhexyl)indocyanine dye (NIRD) was prepared by the reaction of 1,1,2-trimethyl-[1H]-benz[e]indole (20 g, 95.6 mmoles) and 6-bromohexanoic acid (28.1 g, 144.1 mmoles) in 1,2-dichlorobenzene (DCB) at 110° C. for 12 hours. The green solution was cooled to room temperature and the brown solid precipitate formed was collected by filtration. After washing the solid with DCB and diethyl ether, the brown powder obtained (24 g, 64%) was dried under vacuum at room temperature. A portion of this solid (4.0 g,; 9.8 mmoles), glutaconaldehyde dianil monohydrochloride (1.4 g, 5 mmoles) and sodium acetate trihydrate (1.8 g, 12.9 mmoles) were refluxed in ethanol for 1 hour. After evaporating the solvent, 20 mL of a 2N aqueous HCl solution was added to the residue and the mixture was centrifuged and the supernatant was decanted. This procedure was repeated until the supernatant became nearly colorless. About 5 mL of a mixture of water:acetonitrile (3:2) was added to the solid residue which was lyophilized to obtain about 2 g of dark green flakes. Purity of the compound was established with $^1$H-NMR and LC-mass spectrometry.

(c) Dye-peptide conjugate: The dye (60 mg, 75 micromoles) was added to an activation reagent consisting of 0.4 mL HBTU in DMSO (0.2 M) and 0.4 mL diisopropylethylamine in DMSO (0.4 M). The activation was complete in about 30 minutes and the resin-bound peptide (25 micromoles) was added to the dye. The reaction was carried out at room temperature for 3 hours. The mixture was filtered and the solid residue was washed with DMG, acetonitrile and THF. After drying the green residue, the aspartic acid side chain protecting group and peptide cleavage from the resin were accomplished in one step with a mixture of 85% trifluoroacetic acid, 5% water, 5% thioanisole and 5% phenol. The resin was filtered and cold t-butyl methyl ether (MTBE) was used to precipitate the dye-peptide conjugate which was lyophilized and purified by HPLC. Two compounds, mono- and bis-aspartimides of dodecaaspartic acid, were obtained.

Figure 10:
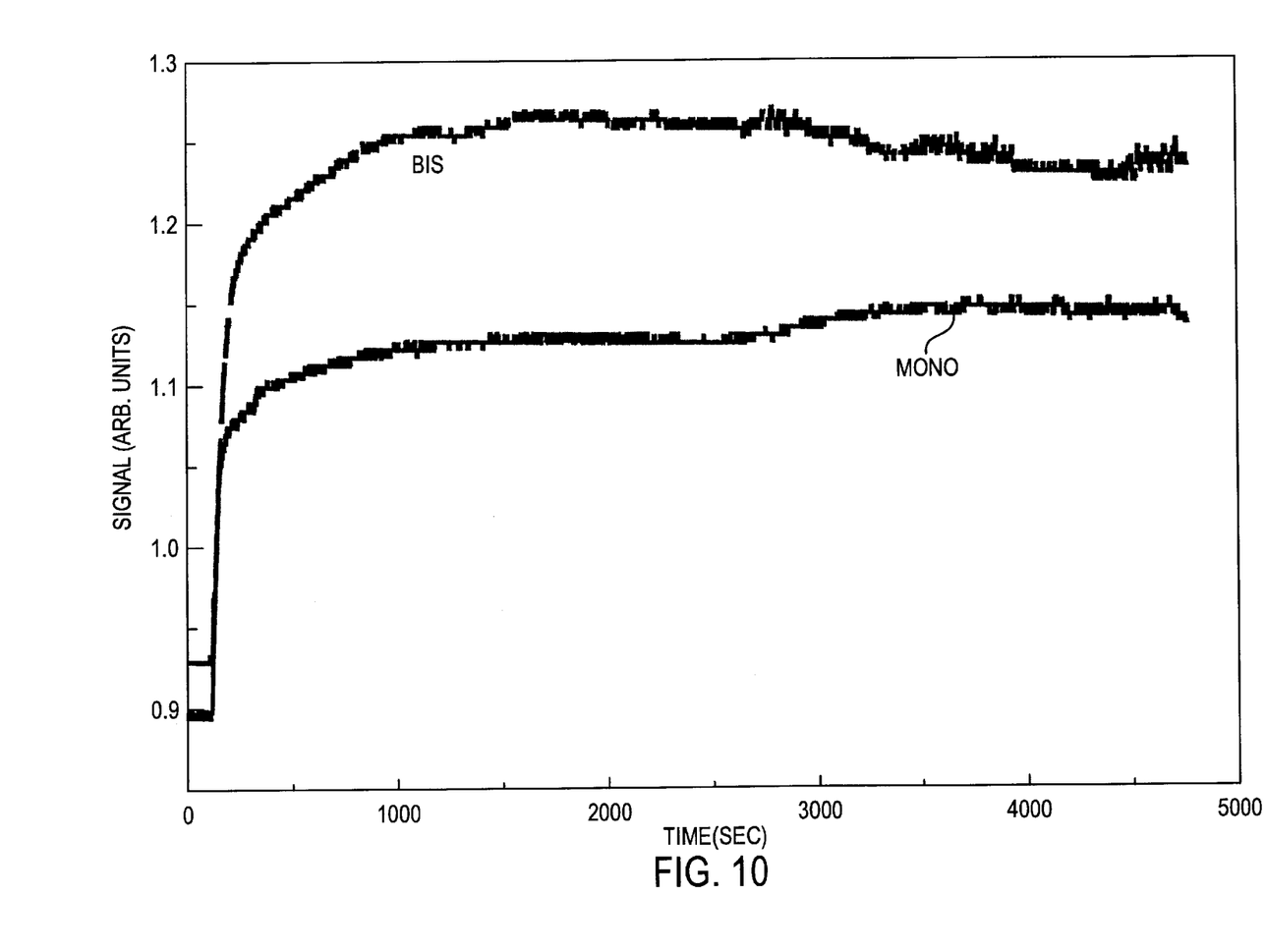
FIG. 10 shows the blood clearance profile of indocyanine-mono(polyaspartic acid 2000) and indocyanine-bis (polyaspartic acid 2000).

The procedure of Example 1 was followed using an excitation wavelength of 780 nanometers and an emission wavelength of 830 nanometers. FIG. 10 shows the blood clearance profile of indocyanine-mono(polyaspartic acid 6000).

EXAMPLE 8

Preparation of Indocyanine (NIRD)-polyaspartic Acid 6000 Conjugate

Figure 11:
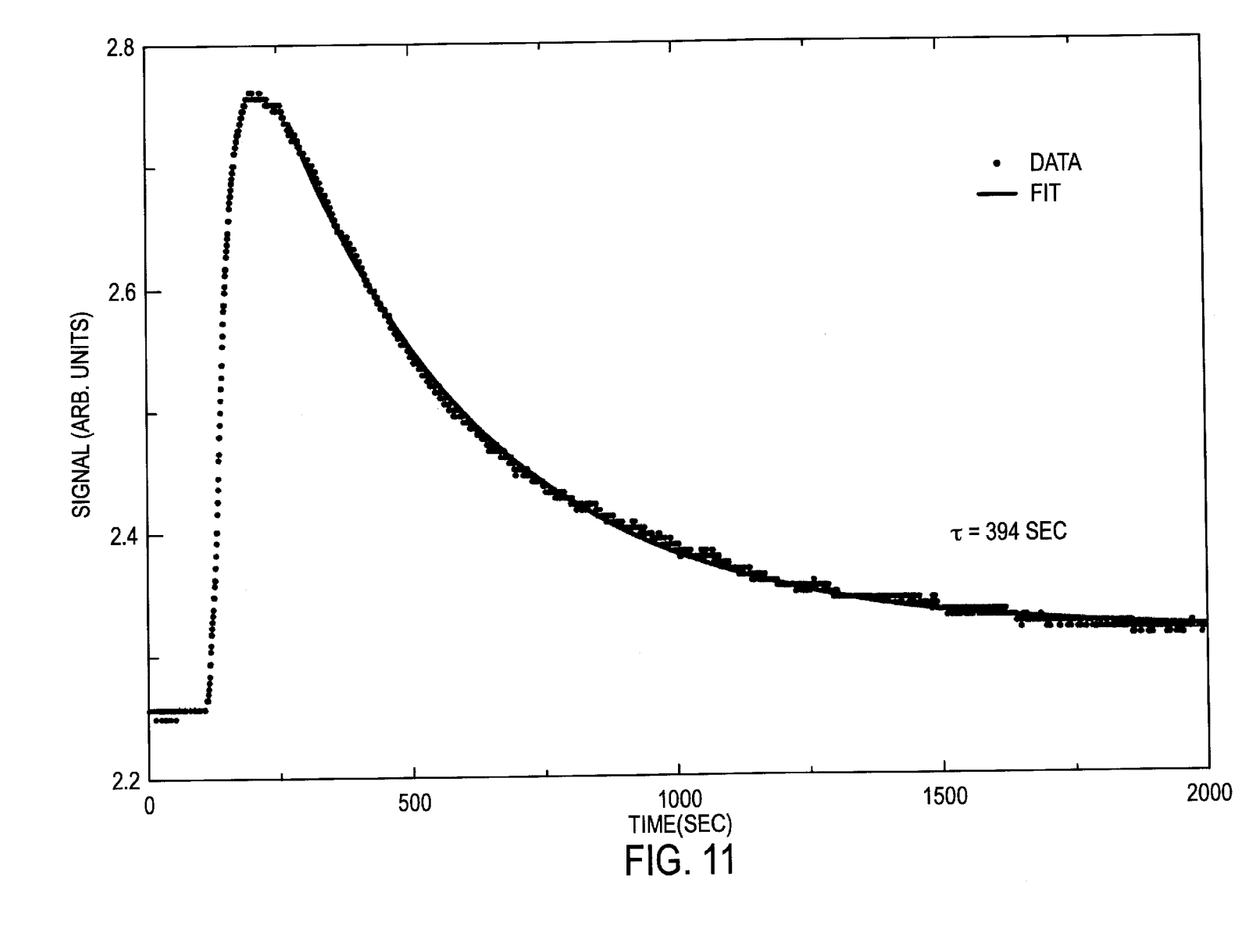
FIG. 11 shows the blood clearance profile of indocyanine (polyaspartic acid 6000).

NIRD (60 mg, 75 micromoles) was activated with a mixture of 0.4 mL HBTU in DMSO (0.2 M) and 0.22 mL diisopropylethylamine in DMSO (0.4 M) for 1 hour. Polyaspartic acid (6 kDa, 100 mg) was added to the dye and the conjugation was complete after 3 hours. Cold MTBE was added (4×10 mL) to precipitate the peptide conjugate and wash off reaction solvents and reagents. The green paste obtained was dissolved in water and lyophilized to give a green solid. The compound was purified by gel filtration chromatograph with Pharmacia PD-10 column (Sephadex G-25) by eluting with PBS. The product was lyophilized and analyzed by HPLC, UV-visible spectrophotometry, fluorometry and mass spectrometry. The procedure of Example 1 was followed using an excitation wavelength of 780 nanometers and an emission wavelength of 830 nanometers. FIG. 11 shows the blood clearance profile of indocyanine (polyaspartic acid 6000).

The utility of non-invasive fluorescence detection to monitor liver or kidney function has been established.

The steps of the invention may be repeated in order to determine if physiological function is changing.

Indocyanine green is a dye which fluoresces at a wavelength of about 830 nm and was used to measure the physiological function of the liver. In order to measure the physiological function of the liver, a body portion was irradiated with light with a wavelength of about 780 nm. The physiological or hepatic function of liver cells was measured using the claimed method.

Fluorescein labeled, succinylated poly-D-lysine is a dye which fluoresces at a wavelength of about 518 nm and was used to measure the physiological function of the kidneys. In order to measure the physiological function of the kidneys, a body portion was irradiated with light with a wavelength of about 488 nm. Renal function was measured using the above-described method of the invention. See FIG. 2.

The dyes were intravenously injected. A body portion, which included blood vessels near the surface of the skin, was irradiated with a laser or with infrared radiation.

The claimed invention may also be used to evaluate hypercholesterolemia. Clearance rate measurements may allow the clinician to determine whether high serum cholesterol resulted from increased rate of LDL production or from decreased rate of LDL clearance, which may impact therapy. The claimed invention may also be used to measure cardiac output. The ability to concurrently measure cardiac function while also measuring hepatic and renal function may allow the clinician to draw preliminary conclusions about whether any observed changes in hepatic and renal functions were due to primary renal or hepatic disease or secondary to heart disease.

Since many modifications, variations and changes in detail may be made to the described embodiments, it is intended that all matter in the foregoing description and shown in the accompanying drawings be interpreted as illustrative and not in a limiting sense.

What is claimed is:

1. A method of measuring physiological function of a group of cells in a patient's body selected from the group consisting of renal or hepatic cells comprising the steps of:
   a) selecting a detectable agent which emits an electromagnetic emission, said agent being selectively removed from a body fluid in said patient's body by said group of cells in said patient's body, and wherein said emission occurs in said body fluid in said patient's body;
   b) introducing said agent into said body fluid of a patient, which body fluid contacts said group of cells in said patient's body, and wherein said emission occurs in said body fluid;
   c) measuring said emission from a body portion in said patient's body through which said body fluid passes wherein said emission results from agent not yet removed from said body fluid at a time of said measuring; and
   d) determining said physiological function based on measurement of said emission,
   wherein said agent is a dye conjugated to a physiologically acceptable polyanionic carrier to form a dye-polyanionic carrier conjugate which fluoresces at a first wavelength upon being irradiated with light of a second wavelength and wherein said dye-polyanionic carrier conjugate is selected from the group consisting of:

Fluorescein-polyaspartic acid,
Fluorescein-polyglutamic acid,
Fluorescein-polyacrylic acid,
Fluorescein-polynucleotides,
Fluorescein-polynitrophenylalanine,
Fluorescein-polydinitrophenylalanine,
Fluorescein-polytrinitrophenylalanine,
Fluorescein-polysulfonylphenylalanine,
Fluorescein-polydisulfonylphenylalanine,
Fluorescein-polytrisulfonylphenylalanine,
Fluorescein-polymalonate,
Fluorescein-polyglutarate,
Fluorescein-polyglycolate,
Bis(hexanoic acid)indocyanine green-polyaspartic acid,
Bis(hexanoic acid)indocyanine green-polyglutamic acid,
Bis(hexanoic acid)indocyanine green-polyacrylic acid,
Bis(hexanoic acid)indocyanine green-polynucleotides,
Bis(hexanoic acid)indocyanine green-polynitrophenylalanine,
Bis(hexanoic acid)indocyanine green-polydinitrophenylalanine,
Bis(hexanoic acid)indocyanine green-polytrinitrophenylalanine,
Bis(hexanoic acid)indocyanine green-polysulfonylphenylalanine,
Bis(hexanoic acid)indocyanine green-polydisulfonylphenylalanine,
Bis(hexanoic acid)indocyanine green-polytrisulfonylphenylalanine,
Bis(hexanoic acid)indocyanine green-polysuccinate,
Bis(hexanoic acid)indocyanine green-polymalonate,
Bis(hexanoic acid)indocyanine green-polyglutarate,
Bis(hexanoic acid)indocyanine green-polyglycolate,
Bis(propanoic acid)indocyanine green-polyaspartic acid, Bis(propanoic acid)indocyanine green-polyglutamic acid,
Bis(propanoic acid)indocyanine green-polyacrylic acid,
Bis(propanoic acid)indocyanine green-polynucleotides,
Bis(propanoic acid)indocyanine green-polynitrophenylalanine,
Bis(propanoic acid)indocyanine green-polydinitrophenylalanine,
Bis(propanoic acid)indocyanine green-polytrinitrophenylalanine,
Bis(propanoic acid)indocyanine green-polysulfonylphenylalanine,
Bis(propanoic acid)indocyanine green-polydisulfonylphenylalanine,
Bis(propanoic acid)indocyanine green-polytrisulfonylphenytalanine,
Bis(propanoic acid)indocyanine green-polysuccinate,
Bis(propanoic acid)indocyanine green-polymalonate,
Bis(propanoic acid)indocyanine green-polyglutarate,
Bis(propanoic acid)indocyanine green-polyglycolate,
Bis(benzothiazole)squaraine-polyaspartic acid,
Bis(benzothiazole)squaraine-polyglutamic acid,
Bis(benzothiazole)squaraine-polyacrylic acid,
Bis(benzothiazole)squaraine-polynucleotides,
Bis(benzothiazole)squaraine-polynitrophenylalanine,
Bis(benzothiazole)squaraine-polydinitrophenylalanine,
Bis(benzothiazole)squaraine-polytrinitrophenylalanine,
Bis(benzothiazole)squaraine-polysulfonylphenylalanine,
Bis(benzothiazole)squaraine-polydisulfonylphenylalanine,
Bis(benzothiazole)squaraine-polytrisulfonylphenylalanine,
Bis(benzothiazole)squaraine-polysuccinate,
Bis(benzothiazole)squaraine-polymalonate,
Bis(benzothiazole)squaraine-polyglutarate,
Bis(benzothiazole)squaraine-polyglycolate,
Bis(trihydroxyphenyl)squaraine-polyaspartic acid,
Bis(trihydroxyphenyl)squaraine-polyglutamic acid,
Bis(trihydroxyphenyl)squaraine-polyacrylic acid,
Bis(trihydroxyphenyl)squaraine-polynucleotides,
Bis(trihydroxyphenyl)squaraine-polynitrophenylalanine,
Bis(trihydroxyphenyl)squaraine-polydinitrophenylalanine,
Bis(trihydroxyphenyl)squaraine-polytrinitrophenylalanine,
Bis(trihydroxyphenyl)squaraine-polysulfonylphenylalanine,
Bis(trihydroxyphenyl)squaraine-polydisulfonylphenylalanine,
Bis(trihydroxyphenyl)squaraine-polytrisulfonylphenylalanine,
Bis(trihydroxyphenyl)squaraine-polysuccinate,
Bis(trihydroxyphenyl)squaraine-polymalonate,
Bis(trihydroxyphenyl)squaraine-polyglutarate, and
Bis(trihydroxyphenyl)squaraine-polyglycolate;

wherein prior to said measuring step, said body portion through which said body fluid passes is irradiated with said light of said second wavelength, causing said dye-polyanionic carrier conjugate to fluoresce at said first wavelength;

wherein said emission being measured is fluorescence of said dye-polyanionic carrier conjugate at said first wavelength; and wherein said determination of physiological function is based on measurement of fluorescence of said first wavelength.

2. A method as defined by claim 1, wherein steps b) through d) are repeated to determine if physiological function changes.

3. A method as defined by claim 1, wherein said agent is injected.

4. A method as defined by claim 1, wherein said agent is intravenously injected.

5. A method as defined by claim 1, wherein said body portion includes blood vessels near a surface of skin of said patient.

6. A method as defined by claim 1, wherein said second wavelength is about 400–1200 nanometers.

7. A method as defined by claim 1, wherein said second wavelength is about 488 nanometers.

8. A method as defined by claim 1, wherein said body portion is irradiated with a laser.

9. A method as defined by claim 1, wherein said body portion is irradiated with infrared radiation.

10. A method as defined by claim 1, wherein said body cells are kidney cells.

11. A method as defined by claim 1, wherein said body cells are liver cells.

12. A method as defined by claim 1, wherein said first wavelength is about 830 nanometers.

13. A method as defined in claim 1, wherein said first wavelength is about 518 nanometers.

14. A method as defined by claim 1, wherein said physiological function is renal function.

15. A method as defined by claim 1, wherein said physiological function is hepatic function.

16. A method as defined by claim 1, wherein said emission is measured invasively or non-invasively with respect to said body portion.

17. A method as defined by claim 16, wherein said emission is endoscopically measured.

18. A method as defined by claim 16, further including the step of inserting a catheter into said body portion so as to measure said emission.

19. A method as defined by claim 16, wherein said body portion is an ear of the patient's body.

20. A method as defined by claim 16, wherein said body portion is a finger of the patient's body.

* * * * *